United States Patent [19]

Patrick et al.

[11] Patent Number: 4,515,158
[45] Date of Patent: May 7, 1985

[54] SPEECH PROCESSING METHOD AND APPARATUS

[75] Inventors: James F. Patrick; Peter Seligman; Yit C. Tong; Graeme M. Clark, all of Melbourne, Australia

[73] Assignee: The Commonwealth of Australia Secretary of Industry and Commerce, Canberra, Australia

[21] Appl. No.: 329,986

[22] Filed: Dec. 11, 1981

[30] Foreign Application Priority Data

Dec. 12, 1980 [AU] Australia .............................. 6923/80
Jun. 30, 1981 [AU] Australia .............................. 9509/81

[51] Int. Cl.$^3$ ............................................. A61N 1/36
[52] U.S. Cl. ............................ 128/419 R; 179/107 R
[58] Field of Search .................. 128/784, 786, 419 R; 179/107 R, 107 BC, 107 E

[56] References Cited

U.S. PATENT DOCUMENTS 4,267,410  5/1981  Forster et al. ................. 179/107 BC
4,284,856  8/1981  Hochmair et al. .............. 179/107 E

FOREIGN PATENT DOCUMENTS 2811120  9/1978  Fed. Rep. of Germany ... 128/419 R
2823798  9/1979  Fed. Rep. of Germany ...... 128/784
WO80/02767 12/1980  PCT Int'l Appl. ............. 128/419 R

OTHER PUBLICATIONS

Gheewela et al, "A CMOS Implantable ... ", IEEE J. Solid State Circuits, vol. 10, No. 6, pp. 472–479, Dec. 1975.

Primary Examiner—Lee S. Cohen
Attorney, Agent, or Firm—Walter C. Farley

[57] ABSTRACT

Signal processing system for converting a speech signal into a data signal for controlling a hearing prosthesis having an implanted electrode array adapted to stimulate the auditory nerve fibers of a patient by the application of electrical currents to selected electrodes in the array. The system generates an input signal current corresponding to a received speech signal. The amplitude and frequency of the fundamental voicing component of the speech signal is approximated as are the amplitude and frequency of at least one formant of the speech signal. A programmable microprocessor produces instructions which cause the application of electrical currents to selected groups of electrodes in the array with or without delays between the stimulation of each electrode in the groups. The microprocessor is programmable with data defining a predetermined relationship between each group of electrodes and a selected range of at least one formant frequency and with data defining a predetermined relationship between another formant frequency and the delay between stimulation of each electrode in each said group based on psychophysical testing of the patient. Selection of electrodes based on the estimated frequency of the formants produces the desired percepts in the auditory-like sensations generated in the patient. The microprocessor is further programmable to produce data which determines the level of stimulation of each selected group of electrodes and determines the delay between stimulation of electrodes in each group dependent on the estimated amplitude of formants of the speech signal as well as on predetermined data relating to the sensitivity of each electrode implanted in the patient.

11 Claims, 4 Drawing Figures

SPEECH PROCESSING METHOD AND APPARATUS

The present invention relates to signal processing systems of the type which are suitable for use with implanted hearing prostheses which electronically stimulate the auditory nerves to produce auditory-like sensations.

BACKGROUND OF THE INVENTION

In order to best utilize an auditory prosthesis for speech communication, a signal processor is required which codes the speech signal into a stimulus pattern. Such signal processors in the past have fallen into two general categories:

1. Those which stimulate electrodes in regions where, according to the place-pitch theory of hearing, they would be stimulated in a normal hearing person. Stimulation occurs at rates corresponding to the frequency of vibration of that portion of the basilar membrane.

2. Those which stimulate at one or more positions in the cochlea but with a stimulus common to all electrodes and at a rate equal or proportional to the glottis pulse rate of the speech signal. Whilst speech processors which fall into category 1 provide the formant information of the speech signal, they fail to provide prosodic information. Furthermore, since the spectral energy is distributed over broad peaks, confusing percepts may be heard by the patient. Speech processors which fall into category 2 provide the prosodic information important as an aid to lip reading, but fail to provide the necessary formant frequency information.

The invention which is the subject of PCT/Au80/00016 attempted to overcome these disadvantages by providing a speech processor having an output signal in which both formant and prosodic information is present whereby the production of confusing percepts is avoided.

The speech processor of PCT/Au80/00016 is particularly adapted for use with the implantable hearing prosthesis and the associated stimulation electrode array described in Australian Patent Application Nos. Au-A 41061/78 and AU-A 46563/79 respectively.

The hearing prosthesis includes an electrode processor having an output signal in which both formant and prosodic information is present whereby the production of confusing percepts is avoided.

SUMMARY OF THE INVENTION

Briefly described, in one aspect the invention includes a signal processing system for converting a speech signal into a data signal for controlling a means for stimulating a hearing prosthesis for an individual patient of the type including an implanted electrode array adapted to stimulate the auditory nerve fibers of a patient by the application of sets of electrical currents to selected electrodes in the array. The processing system includes means for receiving a speech signal and for generating an electrical input corresponding to the received speech signal and means for generating from the input signal electrical signals characterizing acoustic features of the speech signal. A programmable means obtains and stores, from the electrical signals, data representative of a relationship between said acoustic features as represented by the signals and sets of electric current stimuli to be applied to the electrode array. Finally, instruction signals are produced for controlling the application of said sets of stimuli by the means for stimulating wherein a stimulus set comprises at least two current pulse stimuli applied sequentially to at least two electrodes, and wherein the sets of stimuli are applied at a rate derived from the voicing frequency of the speech signal for voiced utterances and at a rate independent of the voicing frequency for unvoiced utterances.

Another aspect of the invention comprises a method of producing electrical current signals for selective application to electrodes in an array of electrodes implanted in a patient forming a hearing prosthesis in response to a speech signal to thereby stimulate the auditory nerve fibers of a patient in which the steps include forming an electrical input signal corresponding to the speech signal, producing from the input signal a fundamental signal representative of the amplitude and frequency characteristics of a first formant of the speech signal, defining a predetermined relationship between each of a plurality of groups of electrodes and a selected frequency band of the formant frequency and storing data representative thereof, producing from the input signal a second signal representative of the amplitude and frequency of a second formant of the speech signal, defining a predetermined relationship between the frequency characteristics of the second signal and the electrode sharpness response determined by psychophysical testing of the patient and storing data representative thereof, selecting electrodes to be stimulated based on the correlation between the frequency of the first and second signals and the electrode response so that stimulation thereof can produce desired percepts in the auditory-like sensations generated in the patient, determining the level of stimulation of each selected group of electrodes as a function of the amplitudes of the first and second signals and the loudness of the auditory-like sensation generated in the patient and the delay to be used between stimulation of electrodes in each group as a function of the formant signal frequencies and the sharpness response of each electrode implanted in the patient and storing data representative thereof, and applying current signals at a rate proportional to the voicing frequency to the selected electrode groups in accordance with the stored data and with the defined delay factors between stimulation of individual electrodes in each group.

BRIEF DESCRIPTION OF THE DRAWINGS

In order that the manner in which various advantages are attained in accordance with the invention can be understood in detail, embodiments thereof will be described with reference to the accompanying drawings, which form a part of this specification, and wherein.

DESCRIPTION OF THE PREFERRED EMBODIMENTS

Figure 1:
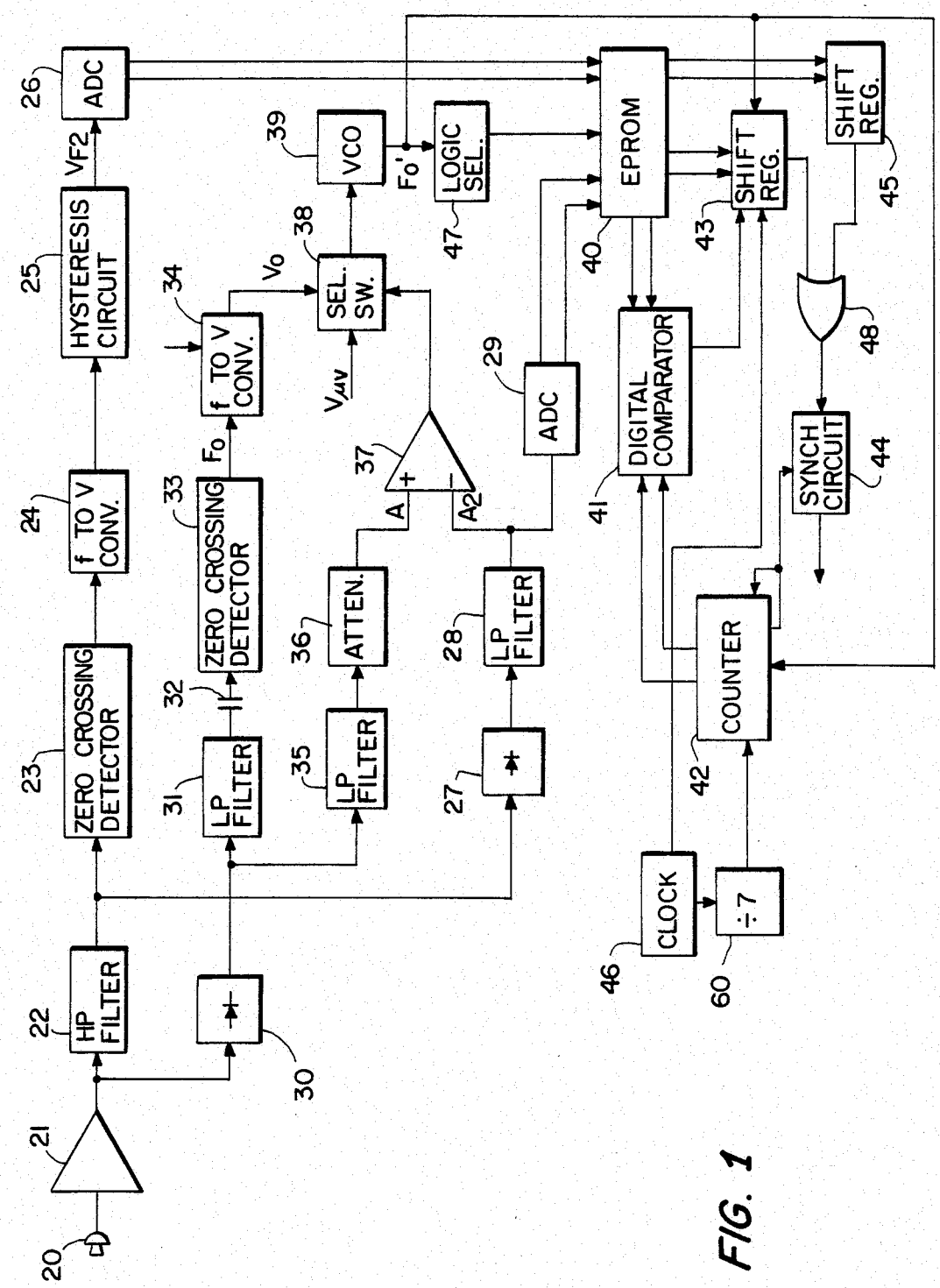
FIG. 1 is a schematic block diagram of a processor apparatus in accordance with the invention.

The speech processor according to the invention is particularly adapted for use with the implantable hearing prosthesis and the associated stimulation electrode array described in Australian Patent Application Nos. AU-A 41061/78 and AU-A 46563/79 respectively.

As described in the earlier Applications referred to above, the hearing prosthesis includes an electrode array which is implanted within the scala tympani region of the cochlea so as to cause stimulation of the auditory nerve fibres by the application of electrical currents of varying levels of intensity and stimulation frequency. Psychophysical tests are used to determine the sharpness ranking of each electrode and a programmable means within the speech processor is programmed to cause stimulation of selected electrodes depending on the characteristics of at least one of the time varying parameters which essentially described the speed signal within any defined time period.

Essentially the speech processor PCT/Au80/00016 comprises a signal processing system for converting a speech signal into a data signal for controlling a hearing prosthesis including an implanted electrode array adapted to stimulate the auditory nerve fibres of a patient by the application of electrical currents to selected electrodes in said array, said processing system comprising means for generating an input signal corresponding to a received speech signal, means for estimating the amplitude and frequency of the fundamental voicing component of said speech signal, means for estimating the amplitude and frequency of the second formant component of said speech signal, means for determining whether said speech signal is voiced or unvoiced, progrmmable means for producing instruction data which in use causes the application of said electrical currents to selected electrodes in said array, said programmable means being programmed with data (FIG. 2) defining a predetermined relationship between each electrode and a selected range of said second formant frequencies based on psychophysical testing of the patient and causing selection of said electrodes based on the estimated frequency of said second formant component such as to produce the desired percepts in the auditory-like sensations generated in the patient, means for causing stimulation of said selected electrode at a frequency dependent on the estimated frequency of said fundamental voicing component for voiced speech signals and at a lower substantially constant frequency for unvoiced speech signals, said programmable means further being programmed to produce data which determines the level of stimulation of each selected electrode dependent on said estimated amplitude of said second formant component of said speech signal as well as on predetermined data relating to the sensitivity of each electrode implanted in the patient.

The processor of PCT/Au80/00016 was based on the discovery that amplitudes and frequencies of the fundamental voicing component and the second formant component of the speech signal may be successfully used to essentially define the speech signal for utilization by the prosthesis to cause stimulation of the auditory nerves within a patient to produce auditory-like sensations. To achieve this end, the estimated second formant frequency is mapped so that selected segments of the range of second formant frequencies usually experienced are associated with individual electrodes in the array. The mapping is preferably arranged so that the higher levels of the second formant frequency are associated with the electrodes having greater sharpness ranking and the electrodes in the array are then selected according to the map for stimulation as the second formant frequency is estimated. Electrode selection is achieved by programming the programmable means for each particular patient in accordance with the second formant frequency/sharpness map referred to above. The level of stimulation of each electrode and hence the loudness of the corresponding auditory sensation is determined by the estimated amplitude of the second formant component.

Because of current spread inside the cochlea the number of electrodes providing independent stimulation to different groups of nerve fibres is strictly limited. Thus the number of frequency ranges that can be used to stimulate the electrodes is relatively small. Thus the patients ability to perceive a wide range of speech signals is limited because of the limitations of the processor to break the speech signals of one speech formant down into a sufficient number of frequency ranges to ensure that heard speech can be rendered into an intelligible form for deaf patients.

It is an object of this invention to provide a means of increasing the number of frequency ranges which can be converted into separate stimuli for the brain.

To this end the present invention provides an improvement in the speech processor of PCT/Au80/00016 wherein the programmable means is able to produce instruction data to cause application of electric current to more than one electrode for any one received signal. The received signal may be a single pulse or a pulse train consisting of a number of pulse segments and with the present invention each of these pulses or pulse segments is broken into two portions one of which is delayed.

Experiments have shown however, that if two electrodes are stimulated by an interleaved pulse train having the same pulse rate, but with one pulse train delayed relative to the other by up to the pulse period, then sensations which are intermediate between those produced by stimulating either electrode alone can be elicited. The sensation produced depends on the delay time and the amplitudes of the two pulse trains.

This interleaved pulse train technique is used by this invention in addition to single electrode stimuli to provide a means of increasing the number of frequency or bands which can be presented as separate stimuli to the brain. This invention therefore greatly increases the capability of the patient to interpret speech as compared to prior art processes.

By programming the programmable means, (micro processor) two means for stimulating separate electrodes can be activated so that the output signal for one speech formant from the programmable means is shared between two electrodes.

An important aspect of this invention is that simultaneous excitation of two electrodes tends to cloud perception because of interaction of the two electrical currents. Thus the programmable means in response to one received signal stimulates one electrode with a predetermined amplitude and then within 0.2 to 5 milliseconds later stimulates a second electrode with a second predetermined amplitude. By varying the amplitude and duration of each electrode stimulation a larger number of recognizable electrode stimuli are available and this means a greater number of discrete frequency ranges within one speech formant can be used by the deaf patient to obtain a greater degree of intelligible data.

As in the processor of PCT/Au80/00016 the second formant frequency is mapped so that a selected segment of the frequency range corresponds to a particular combination of sequential stimulation of two electrodes with the same or different amplitude at each electrode. By varying the amplitude at one electrode a different frequency segment can be represented. When varying amplitude at one electrode, change in loudness will be experienced unless the amplitude of the other electrode is also altered to retain the same overall amplitude. Variation of this delay can also be used to distinguish between frequency segments.

It must be noted that the delay between electrode stimulations must be less than the period of output signals from the programmable means. With high frequency segments a shorter delay between electrode stimulation is needed. A preferred delay period for all frequency segments is 0.5 milliseconds.

Another aspect of the present invention is based on the discovery that percepts produced by electrical stimulation of pairs of electrodes implanted in the cochlea can have two formant components. The two physical dimensions corresponding to the placement of the two electrodes were related to the two percept dimensions. This can be interpreted as an analogy to the correspondence between two speech formant frequencies in an acoustic presentation and the two dimensions of the resulting percepts.

It is anticipated that sets of stimuli presented to combinations of three or more electrodes may be used to produce percept analogues to those produced by acoustic signals comprising three or more speech formants.

Therefore, it is possible to map out the correllation of frequencies of two speech formants and through psychophysical testing using electrical stimulation of two electrodes establish a corresponding two values for electrode stimulation which produces a percept analogue to the acoustic presentation of the two speech formants. This enables a speech processor to be programmed to produce a given set of pulses to a pair of electrodes in respect to a received acoustic speech signal, to produce a percept analogue to said acoustic signal.

To this end the present invention provides an improvement to the speech processor of PCT/Au80/00016 wherein the means for generating an input signal corresponding to a received speech signal generates a signal having a plurality of formant components and wherein means are provided for estimating the amplitude and frequency of pairs of formant components and wherein the programmable means is able to produce instruction data to cause application of electric current to pairs of electrodes for any one received signal.

The electric current applied to pairs of electrodes may be applied simultaneously to said electrodes or may be separated by an interval which is small in relation to the average delay between the input in relation to the average delay between the input signals (either a pulse or pulse train) themselves. This delay may be of the order of 0.2 to 5 milliseconds.

In this way by stimulating two electrodes with currents to produce in the patient's brain a percept analogue to a speech signal containing a pair of formant components a more complex percept can be simulated.

For example, by psychophysical testing to determine percept analogues to speech signals comprising the second and third voicing formants, the computer in the speech processor can be appropriately programmed to produce the percept analogues on receipt of the appropriate input signal. Basically the processor of Au80/00016 has been modified by adding means to accommodate at least one additional digital word input and means to stimulate two electrodes from one received signal.

It will be appreciated that in speech, some sounds are unvoiced: they are not produced by a vibration of the glottis, but merely by the movement of the air. Thus, in order to produce the necessary perception of realistic auditory-like sensations within the patient, the speech processor may include means to determine whether the speech signal is voiced or unvoiced at any one time. For this reason, the speech processor may be provided with means for detecting whether the speech signal is voiced or unvoiced and for causing the programmable means to output data to cause stimulation of the selected electrode at a pulse rate which is related to the estimated frequency of the fundamental voicing component of the speech signal for voiced speech components. Where unvoiced speech components are detected, the selected electrodes are stimulated at a lower constant pulse rate which results in a rough sounding percept akin to the unvoiced sound.

Detection of the voiced or unvoiced nature of the speech signal may be achieved by programming the programmable device to compare the instantaneous values of the second formant frequency and the amplitude of the fundamental voicing component.

Alternatively, this decision may be made by comparing the low frequency signal energy with the simultaneous high frequency energy.

It has been discovered that the perception of unvoiced signals may also be learnt by the patient. It has now been discovered that if means for sensing whether a signal is voiced or unvoiced are omitted then a voiced signal will produce recognizable signals while an unvoiced signal will produce random signals which can easily be distinguished by a patient as being an unvoiced signal. This discovery enables one component of the prior art speech processor to be omitted and thus saves space and cost.

A further aspect of this invention relates to means for providing additional data to the brain relating in response to one speech signal. The number of electrodes implantable in the cochlea is limited. By providing electrical current to two electrodes it is possible to achieve a greater variety of signals that can be discriminated by the brain. Where a pulse is received containing two speech formants, two electrodes can be stimulated with current values to give a percept analogue to those two formants. As mentioned above it is possible to provide an interval between the two electrode currents.

It has now been discovered that this interval itself can be perceived by the brain and thus can provide information relating to a further speech formant component. For example if the positions of the electrodes selected provide the analogue to the second and third speech formants, then the interval between the current application to the electrodes of any given pair may correspond to an analogue of the first speech formant F1. Because the frequency ranges of the higher speech formants are usually too high to enable detection by the patient of an interval, this mode of presentation is preferably restricted to the first speech formant F1.

In addition the base interval between the pulses themselves can also be patterned to provide an analogue to the glottal pulse rate (fundamental speech formant F0). Thus, the amplitude of the pulses to each electrode, and the interval between pulses on each electrode and the interval between each electrode being stimulated, can carry speech analogue information.

A preferred embodiment of this invention is as shown in FIG. 1 of the drawings.

Referring to the drawings, the simple hard-wired speech processor shown in block diagram form is designed to implement with a minimum hardware and power consumption a speech processing strategy based on the presentation of the amplitude and frequency of the second formant only of the speech signal, which is represented by stimulation of two electrodes at a predetermined time interval apart at a rate proportional to the frequency of the fundamental voicing component (glottal pulse frequency F0).

The system shown includes a microphone 20 for receiving the speech signal and a preamplifier-/automatic gain control circuit 21 which maintains the output peak signal level nearly constant over a wide range of input signal amplitudes. The second formant frequency F2 is estimated from the output of the circuit 21 by means of a high pass filter 22, a zero crossings detector 23, a frequency to voltage converter 24 and a hysteresis circuit 25 which produces a voltage VF2 proportional to F2, following which the voltage is converted to a five bit digital form by an analogue to digital converter 26. The high pass filter 22 is a two pole high pass filter having a 1500 Hz cutoff and a $Q=2$. The filter has a skirt characteristic which effectively ensures that undesirable contributions to $F_2$ by the first and third formants can be ignored by the zero crossings counter and the RMS circuit. This ensures that $F_2$ dominates any contributions by the other components. The amplitude A2 of the second formant is extracted from the output of the filter 22 by means of a rectifier 27 and a 35 Hz low pass filter 28.

The resulting signal is converted to a five bit digital signal by an analogue to digital converter 29.

The frequency F0 of the fundamental voicing component of the speech signal is extracted from the circuit 21 by a rectifier 30, and a 270 Hz low pass filter 31 which together constitute an envelope detector. The undulations of the envelope are separated from the DC level by a capacitor 32, and the zero crossings of the envelope are detected by circuit 33, following which the frequency of the zero crossings is converted to a voltage V0 by a frequency to voltage converter 34.

To establish whether the speech signal is voiced or unvoiced, the amplitude of the signal from rectifier 30 is measured by a 35 Hz low pass amplitude filter 35 following which it is passed via an attenuator 36 to one input of a comparator 37. As described above, a second is characteristically unvoiced if its high frequency energy is high compared to its low frequency energy. Thus, by adjusting the attenuator 36, the comparator 37 can be made to produce a high output for a voiced signal and a low output for an unvoiced signal.

When the output of the comparator 37 goes high, it actuates a selector switch 38 to pass the voltage V0 from the glottal pulse rate extraction path, and when the output of the comparator 37 goes low, a constant low voltage Vuv is passed to cause stimulation of the implanted electrodes at a low pulse rate, thus producing in the patient a sensation akin to sibilance.

A voltage controlled oscillator 39 converts the output from the selector switch 38 to a frequency corresponding to the rate of stimulation $F_0'$.

The digital amplitude and frequency data corresponding to the amplitude and frequency of the second formant (A2, F2) are fed to a 16 k programmable and erasable read only memory (EPROM) 40. This device accepts the eleven bit input and provides two four bit words corresponding to an electrode number and its level of stimulation. It also accepts through the logic selector 47 an 11 bit input relating to the first or second output word and this information is held in separate parts of the memory of ROM 40. The simple selection logic is an integral part for the provision of multiple channel stimulation. As in PCT/Au80/00016 information included in FIGS. 2, 3 and 4 of that specification is programmed into the EPROM 40 so that the two four bit words designate the selected electrode and the desired level of stimulation of those electrodes. By using two electrodes to represent the second speech formant frequencies falling between those detectable when only one electrode is stimulated, permits those intermediate frequencies to be detected. In this way a patient can be taught to perceive a greater number of second speech formant frequencies and thus improve overall voice perception.

The final operation performed by the processor is to code the information into serial data for transmission to the implanted prosthesis. To do this, it is necessary to transmit a synchronization followed by blank seven bit words until the word appropriate to the electrode to be stimulated is reached and then further blank words until 16 words have been transmitted. A second synchronization bit is outputted to initiate stimulation by the implanted prosthesis.

A four bit digital comparator 41 is used to compare the desired electrode number with the output of a mod-16 counter 42. The counter 42 is reset and starts when a scaled "glottal pulse" $F_0'$ is received. The counter 42 counts groups of seven clock pulses from the clock circuit 46 until the right word is reached. The parallel load shift registers 43 and 45 are loaded at the start with the stimulus level and are then enabled and serially output their data with the data from the parallel load shift register 45 being 0.5 m.s. behind that of load shifter 43. This delay in the output from shift register 45 is preprogrammed with the stimulus level. The outputs of shift registers 43 and 45 are combined in an OR gate (block 48) which is then outputted to circuit 44. The data stream has a synchronization bit added by circuit 44 and holds the output in the reset mode until the next scaled "glottal pulse" is received. The clock and serial data signals pass on to amplifiers and modulators for transmission to the implanted prosthesis via the power and data coil units described in further detail in the co-pending PCT application referred to above.

Figure 2:
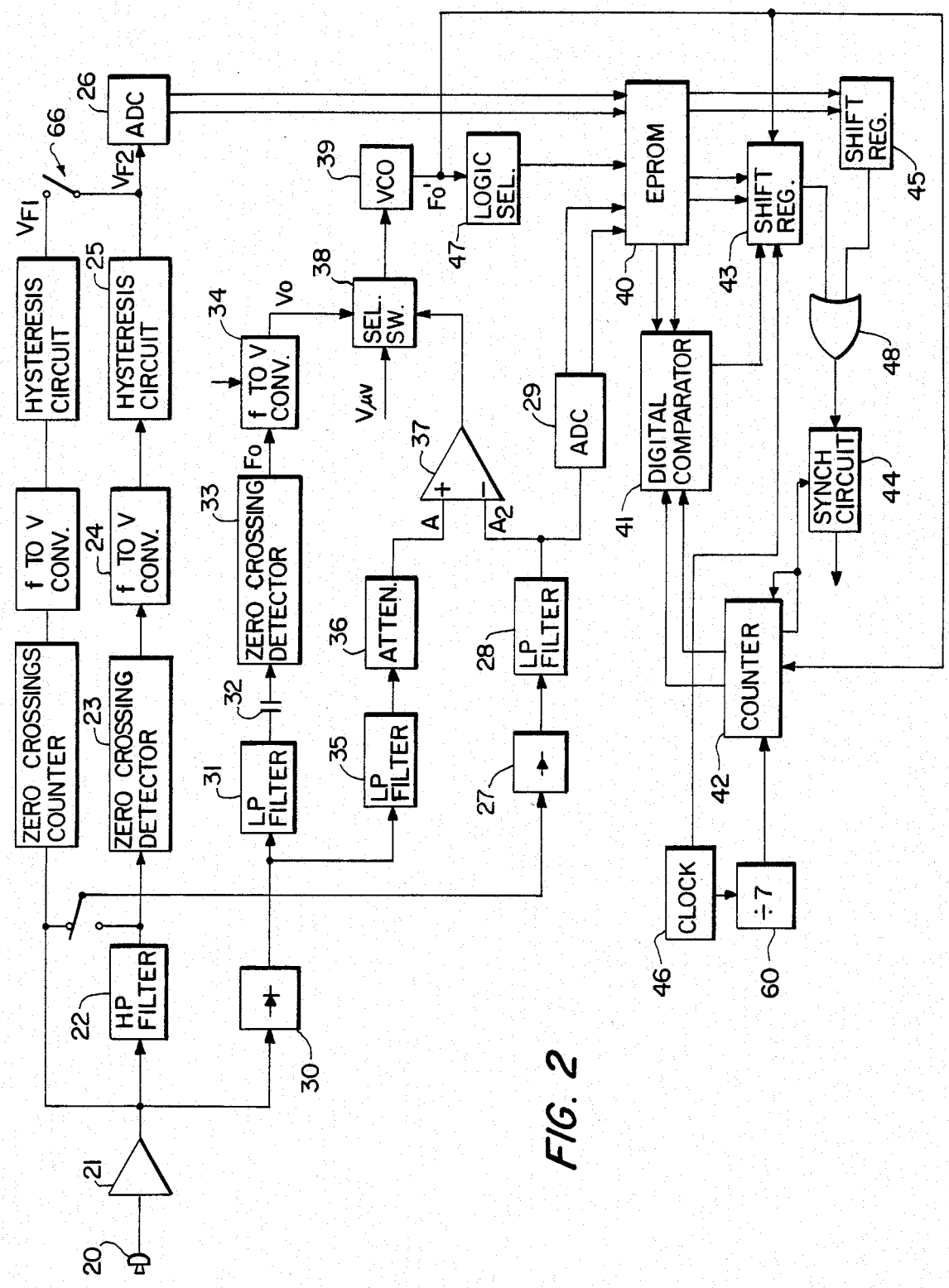
FIG. 2 is a schematic block diagram of a second embodiment of a processor in accordance with the invention.

FIG. 2 represents a modification of the processor illustrated in FIG. 1. In this modification, instead of using the stimulation of two electrodes to increase the range of second speech formant frequencies which can be perceived, information corresponding to analogues of the first speech formant F1 are presented with the second formant to pairs of electrodes.

The modification comprises including after the gain control 21 a switch 62, a zero crossings counter 63, a frequency voltage converter 64, and a hysteresis circuit 65 which produces a voltage VF1 proportional to the first speech formant F1. The switch 66 enables the voltage VF1 to be converted to a five bit digital form by the analogue to digital converter 26. When switch 62 operates the amplitude A1 of the first formant is extracted by means of rectifier 27 and low pass filter 28.

In this way both F1 and F2 analogues can be produced and presented to pairs of electrodes.

Figure 4:
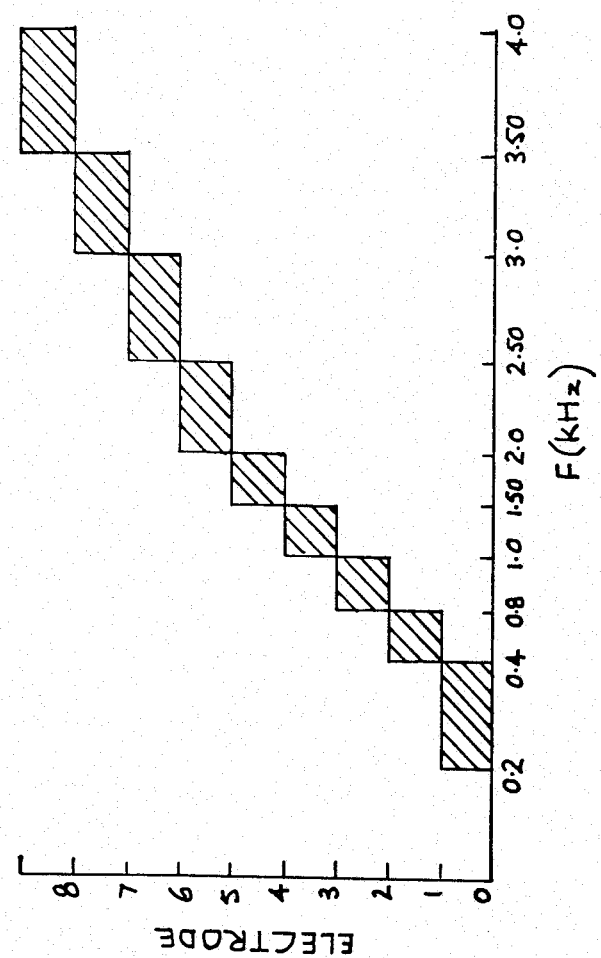
FIG. 4 is a diagram which maps the relationship between the frequency of formants and various electrodes in the hearing prosthesis.

FIG. 4 is a map which relates the frequency F of the first or second formants with the various electrodes in the hearing prosthesis. Where two electrodes are being stimulated to allow perception of F1 and F2 analogues the following rules must apply:

F2>F1 when F2=F1 no differentiation of F1 and F2 can be achieved.

Figure 3:
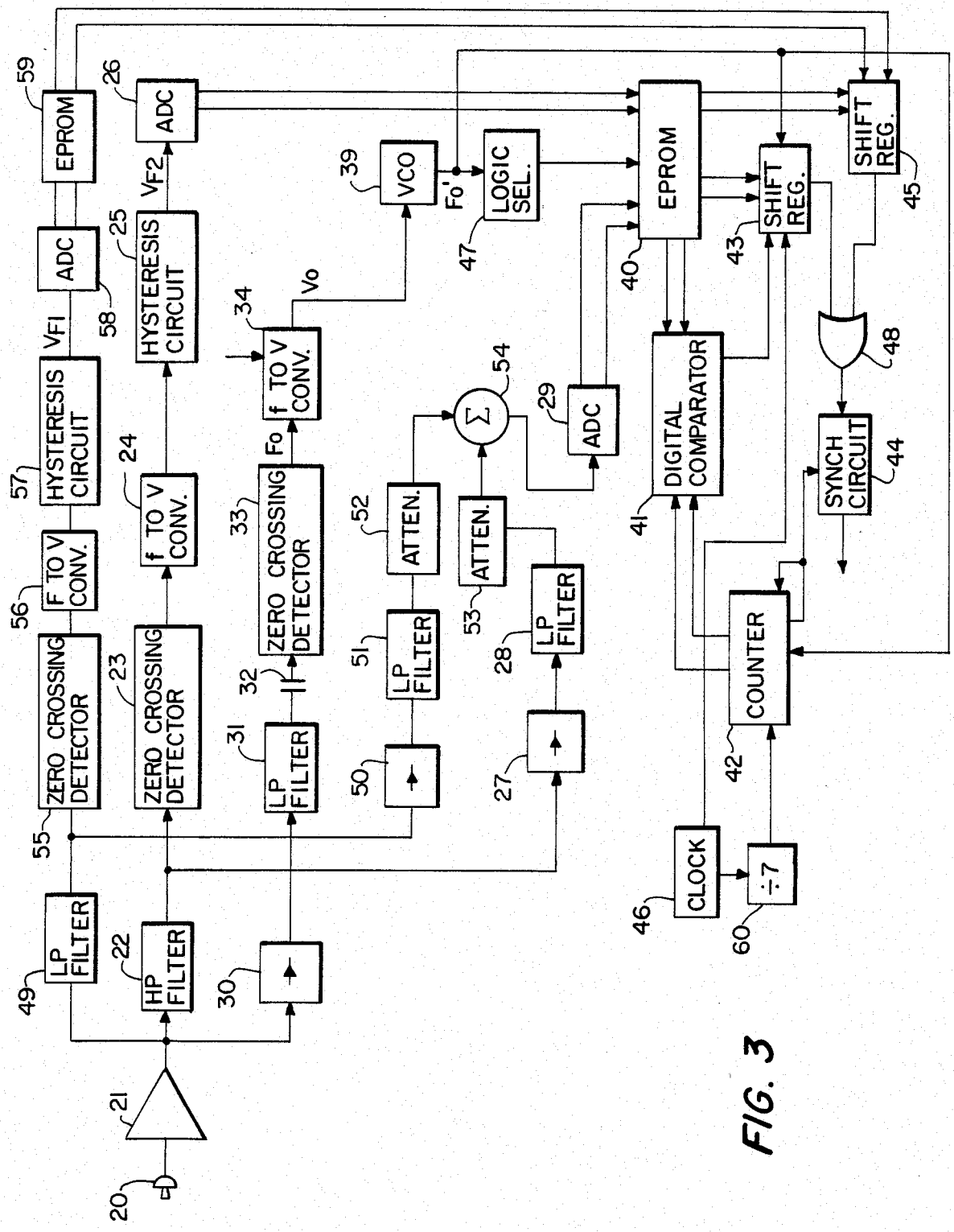
FIG. 3 is a schematic block diagram of a third embodiment of a speech processor in accordance with the invention.

In FIG. 3 an advanced form of the invention is shown as a hardwired speech processor. The components 20 to 28 are identical to those described with reference to FIG. 1.

In this embodiment additional formant frequencies are analysed to provide a more comprehensive analogue signal. This embodiment also presents an alternative to the FIG. 2 embodiment's mode of presenting the first formant analogue.

The amplitude A1 of the first formant is extracted from the output of the filter 49 by means of a rectifier 50 and a low pass filter, 51. A summer 54, adds the outputs of attenuators 52 and 53 to provide an appropriate mixture of the amplitudes A1 and A2 to produce the most natural sounding speech sensations. The resulting signal is converted to a five bit digital signal by an analogue to digital converter 29.

The frequency FO of the fundamental voicing component of the speech signal is extracted from the circuit 21 by a rectifier 30, and a 270 Hz low pass filter 31 which together constitute an envelope detector. The undulations of the envelope are separated from the DC level by a capacitor 32, and the zero crossings of the envelope are detected by circuit 33, following which the frequency of the zero crossings is converted to a voltage $V_o$ by a frequency to voltage converter 34. Subsequently the voltage $V_o$ is converted by voltage frequency converter 39 to frequency $F_O'$ (the scaled glottal pulse).

The digital amplitude and frequency data corresponding to the mixed amplitude (A) and second formant frequency (F2) are fed to a 16 k programmable and erasable read only memory (EPROM) 40. This device accepts the ten bit input and provides two four bit words corresponding to an electrode number and its level of stimulation. It also accepts through the logic selector 47 the eleventh input bit relating to the first or second output word and this information is held in separate parts of the memory of ROM 40 as in the embodiment of FIG. 1.

In order to extract the frequency information on the first formant F1, a low pass filter 49 set at approximately 1000 Hz is employed and this is followed by a zero crossing detector 55, a voltage to frequency converter 56, a hysteresis smoothing circuit 57, and an analogue to digital converter 58, in much the same way as the second formant is extracted, differing basically only in the characteristics of the initial filter.

The means of presentation of the first formant F1 is in the form of a delay between the pulse pairs. This delay is derived from the F1 data via the electrically programmable ROM (EPROM) 59 which is programmed to output delays in the form of a digital quantity appropriate to natural sounding speech as determined by the psychophysical tests.

The remaining functions of the processor are identical to the embodiment described with reference to FIG. 1.

From the above it can be seen that the present invention provides a speech processor that is no longer limited to providing a percept to only a two component speech signal but is able to present a percept analogue of a speech signal having three or more formant components.

We claim:

1. A signal processing system for converting a speech signal into a data signal for controlling a means for stimulating of a hearing prosthesis for an individual patient, the prosthesis being of the type including an implanted electrode array adapted to stimulate the auditory nerve fibers of a patient by the application of electrical currents to selected electrodes in the array, said processing system comprising means for receiving a speech signal and for generating an electrical input signal having a plurality of components corresponding to a plurality of formant components of the received speech signal, first means for generating from said input signal electrical signals representative of at least one of the amplitude and frequency of the fundamental voicing component FO of said speech signal, second means for generating from said input signal electrical signals representative of at least one of the amplitudes or frequencies of a plurality of formants of said speech signal, programmable means for producing instruction signals for controlling the application of sets of electrical signals selected from said signals generated by said first and second means to selected groups of electrodes in said array with selectable delays between the stimulation of each electrode in each of said groups, said programmable means including means for storing data representative of a predetermined relationship between each group of electrodes and a selected range of at least one formant frequency based on psychophysical testing of the patient and data defining a predetermined relationship between another formant frequency and the delay between stimulation of electrodes in each group, said programmable means further including means for producing instruction signals for determining the level of stimulation of each selected group of electrodes as a function of the amplitude of said formants of said speech signal, and storage means for generating and storing stimulus signals corresponding to said instructions and for releasing said signals, separated in time by said selectable delays, to said means for stimulating the selected electrodes.

2. A signal processing system according to claim 1 which includes means for determining whether said speech signal is voiced or unvoiced, said programmable means including means responsive to reception of unvoiced speech signals for controlling said means for stimulating said electrodes to generate signals at a substantially constant frequency lower than the average frequency of said formant.

3. A signal processing system according to claim 1 wherein said programmable means includes means for providing control signals to said means for stimulating the electrodes such that the stimulation of electrode pairs is at a rate proportional to the fundamental voicing component, and for stimulating selected pairs of electrodes with varying current amplitudes to represent the frequency of the second speech formant, the delay between the stimulation of electrode pairs being used to represent the frequency of the first speech formant.

4. A signal processing system as claimed in claim 1 wherein said programmable means includes means for providing control signals for said means for stimulating the electrodes such that the stimulation of electrode pairs is at a rate proportional to the fundamental voicing component and the stimulation of particular electrode pairs causing stimulation of one electrode in a pair represents a frequency of the first speech formant and stimulation of the second electrode represents the frequency of the second speech formant.

5. A method of producing electrical current signals for selective application to electrodes in an array of electrodes implanted in a patient forming a hearing prosthesis in response to a speech signal to thereby stimulate the auditory nerve fibers of a patient comprising forming an electrical input signal corresponding to the speech signal, producing from the input signal a fundamental signal representative of the voicing frequency of the speech signal, producing from the input signal a first signal representative of the amplitude and frequency characteristics of a first formant of the speech signal, defining a predetermined relationship between each of a plurality of groups of electrodes and a selected frequency band of the formant frequency and storing data representative thereof, producing from the input signal a second signal representative of the amplitude and frequency of a second formant of the speech signal, defining a predetermined relationship between the frequency characteristics of the second signal and the electrode sharpness response determined by psychophysical testing of the patient and storing data representative thereof, selecting electrodes to be stimulated based on the correlation between the frequency of the first and second signals and the electrode response so that stimulation thereof can produce desired percepts in the auditory-like sensations generated in the patient, determining the level of stimulation of each selected group of electrodes as a function of the amplitudes of the formant signals and the loudness the auditory-like sensation generated in the patient, and the delay to be used between stimulation of electrodes in each group as a function of the formant signal frequencies and the sharpness response of each electrode implanted in the patient and storing data representative thereof, and applying current signals at a rate proportional to the voicing frequency to the selected electrode groups in accordance with the stored data and with the defined delay factors between stimulation of individual electrodes in each group.

6. A signal processing system for converting a speech signal into a data signal for controlling a means for stimulating of a hearing prosthesis for an individual patient, the prosthesis being of the type including an implanted electrode array adapted to stimulate the auditory nerve fibers of a patient by the application of electrical currents to selected electrodes in the array, said processing system comprising means for receiving a speech signal and for generating an electrical input signal having a plurality of formant components corresponding to the formant components of the received speech signal, first means for generating from said input signal electrical signals representative of at least one of the amplitude and frequency of the fundamental voicing component FO of said speech signal, second means for generating from said input signal electrical signals representative of at least one of the amplitudes and frequencies of a plurality of formants of said speech signal, programmable means for producing instruction signals for controlling the application of sets of electrical signals in a manner determined by said signals generated by said first and second means to selected groups of electrodes in said array with selectable delays between the stimulation of electrodes in each of said groups, said programmable means including means for storing data representative of a predetermined relationship between each group of electrodes and a selected range of at least one formant frequency and data defining a predetermined relationship between another formant frequency and the delay between stimulations of electrodes in each said group based on psychophysical testing of the patient, and selection logic means for selecting the electrodes to be stimulated as a function of the approximated frequency of said formants to produce the desired percepts in the auditory-like sensations generated in the patient, said programmable means further including means for producing and supplying to said means for stimulating instruction signals for determining the level of stimulation of each selected group of electrodes as a function of the amplitude of said formants of said speech signal and determining the delay between the stimulation of individual electrodes in each said group as a function of the formant signal frequencies.

7. A signal processing system for converting a speech signal into a data signal for controlling a means for stimulating of a hearing prosthesis for an individual patient, the prosthesis being of the type including an implanted electrode array adapted to stimulate the auditory nerve fibers of a patient by the application of sets of electrical currents to selected electrodes in the array, said processing system comprising means for receiving a speech signal and for generating an electrical input corresponding to the received speech signal;

means for generating from said input signal electrical signals characterizing acoustic features of the speech signal;

programmable means for obtaining from said electrical signals and storing data representative of a relationship between said acoustic features as represented by said signals and sets of electric current stimuli to be applied to said electrode array; and means for producing instruction signals for controlling the application of said sets of stimuli by said means for stimulating wherein a stimulus set comprises at least two current pulse stimuli applied sequentially to at least two electrodes, and wherein said sets of stimuli are applied at a rate derived from the voicing frequency of the speech signal for voiced utterances and at a rate independent of the voicing frequency for unvoiced utterances.

8. A signal processing system according to claim 7, wherein, for unvoiced utterances, said programmable means controls said means for stimulating to apply the stimulus sets at a substantially constant rate less than the rate of application for any voiced utterance.

9. A signal processing system according to claim 7, wherein said programmable means selects two groups of electrodes for the application of two current stimuli in a stimulus set, where one electrode group is selected on the basis of the frequency of the second formant and the other electrode group is selected on the basis of the frequency of the first formant.

10. A signal processing system according to claim 7, wherein said programmable means selects a group of electrodes for the presentation of a stimulus set comprising two sequential stimulus current pulses based on the frequency of the second formant, the time interval between the application of said two stimuli being dependent upon the frequency of the first formant.

11. A signal processing system according to claim 7, wherein said programmable means selects a group of electrodes for the presentation of a stimulus set comprising two sequential stimulus current pulses having a fixed interpulse delay, where both electrode groups are selected on the basis of the frequency of a single formant.

* * * * *